United States Patent
Mani et al.

(10) Patent No.: US 8,968,326 B2
(45) Date of Patent: Mar. 3, 2015

(54) PNEUMATIC SURGICAL INSTRUMENT AND CORRESPONDING METHODS FOR IMPLANTING ORTHOPEDIC IMPLANTS IN BONE

(76) Inventors: Frederic Mani, Dully (CH); Thierry Monnier, Les Rousses (FR); Alain Lebet, Lausanne (CH)

(*) Notice: Subject to any disclaimer, the term of this patent is extended or adjusted under 35 U.S.C. 154(b) by 183 days.

(21) Appl. No.: 13/467,662

(22) Filed: May 9, 2012

(65) Prior Publication Data

US 2013/0204264 A1 Aug. 8, 2013

Related U.S. Application Data

(63) Continuation-in-part of application No. 13/413,551, filed on Mar. 6, 2012, which is a continuation-in-part of application No. 13/413,455, filed on Mar. 6, 2012.

(60) Provisional application No. 61/596,193, filed on Feb. 7, 2012.

(51) Int. Cl.
  *A61B 17/58* (2006.01)
  *A61B 17/60* (2006.01)
  *A61F 2/00* (2006.01)
  *A61B 17/00* (2006.01)

(52) U.S. Cl.
  USPC .............................. 606/100; 606/99; 606/190

(58) Field of Classification Search
  CPC ..... A61B 17/92; A61F 2/4637; A61F 2/4609; A61F 2/4607
  USPC ........................................... 606/190, 99, 100
  See application file for complete search history.

(56) References Cited

U.S. PATENT DOCUMENTS

| | | | |
|---|---|---|---|
| 2,275,102 A | 3/1942 | Fitzsimmons | |
| 3,250,334 A | 5/1966 | Sussman | |
| 4,016,873 A | 4/1977 | Anderson | |
| 4,131,165 A | 12/1978 | Walker et al. | |
| 4,298,074 A * | 11/1981 | Mattchen | 173/129 |
| 4,399,813 A | 8/1983 | Bawber | |
| 4,462,395 A | 7/1984 | Johnson | |
| 4,476,861 A | 10/1984 | Dimakos | |
| 4,716,890 A | 1/1988 | Bichel | |
| 5,057,112 A | 10/1991 | Sherman | |
| 5,108,400 A | 4/1992 | Appel et al. | |
| 5,160,336 A | 11/1992 | Favre | |
| 5,171,313 A | 12/1992 | Salyor | |
| 5,352,230 A * | 10/1994 | Hood | 606/99 |
| D362,503 S | 9/1995 | Cook et al. | |

(Continued)

FOREIGN PATENT DOCUMENTS

| | | |
|---|---|---|
| EP | 0317507 | 4/1992 |
| EP | 1163862 | 9/2003 |

(Continued)

*Primary Examiner* — David Bates
(74) *Attorney, Agent, or Firm* — Woods Patent Law

(57) ABSTRACT

Various embodiments of components, devices, systems and methods are provided for a pneumatic surgical instrument having a probe or an impactor disposed at a distal end thereof and configured to make contact with a selected portion of an orthopedic implant or device and drive the implant into a hole or void formed in a patient's bone. The instrument is configured to generate a shock wave, which is then transferred to the distal end of the probe or impactor, and hence into the orthopedic implant, thereby causing the implant to be driven into contact with portions of the void or hole.

19 Claims, 19 Drawing Sheets

(56) References Cited

U.S. PATENT DOCUMENTS

| | | |
|---|---|---|
| 5,449,363 A | 9/1995 | Vrust et al. |
| 5,613,483 A | 3/1997 | Lukas et al. |
| 5,626,584 A | 5/1997 | Young |
| 5,906,623 A | 5/1999 | Peterson |
| 5,980,528 A | 11/1999 | Salys |
| 6,152,930 A | 11/2000 | Mastrorio et al. |
| 7,048,073 B2 | 5/2006 | Hezeltine |
| 7,326,217 B2 | 2/2008 | Bubb |
| 7,407,070 B2 | 8/2008 | Hezeltine |
| 7,470,274 B2 | 12/2008 | Lebet |
| 7,485,149 B1 | 2/2009 | White |
| 7,569,057 B2 | 8/2009 | Liu et al. |
| 7,604,637 B2 | 10/2009 | Johnson et al. |
| 7,811,256 B2 | 10/2010 | Landman et al. |
| 2002/0010486 A1 | 1/2002 | Hirt |
| 2003/0000774 A1 | 1/2003 | Highley |
| 2006/0069395 A1 | 3/2006 | Lebet |
| 2006/0100553 A1 | 5/2006 | Lodin |
| 2009/0118741 A1 | 5/2009 | Lebet |
| 2010/0305624 A1 * | 12/2010 | Lozier et al. .......... 606/86 R |
| 2012/0022545 A1 | 1/2012 | Lebet |

FOREIGN PATENT DOCUMENTS

| | | |
|---|---|---|
| EP | 2 502 580 A1 | 9/2012 |
| EP | 13166942.6 | 11/2013 |
| FR | 2 925 841 | 7/2009 |
| WO | WO 95/22934 | 8/1995 |
| WO | WO 98/26705 | 6/1998 |
| WO | WO 2010/109327 A1 | 9/2010 |

* cited by examiner

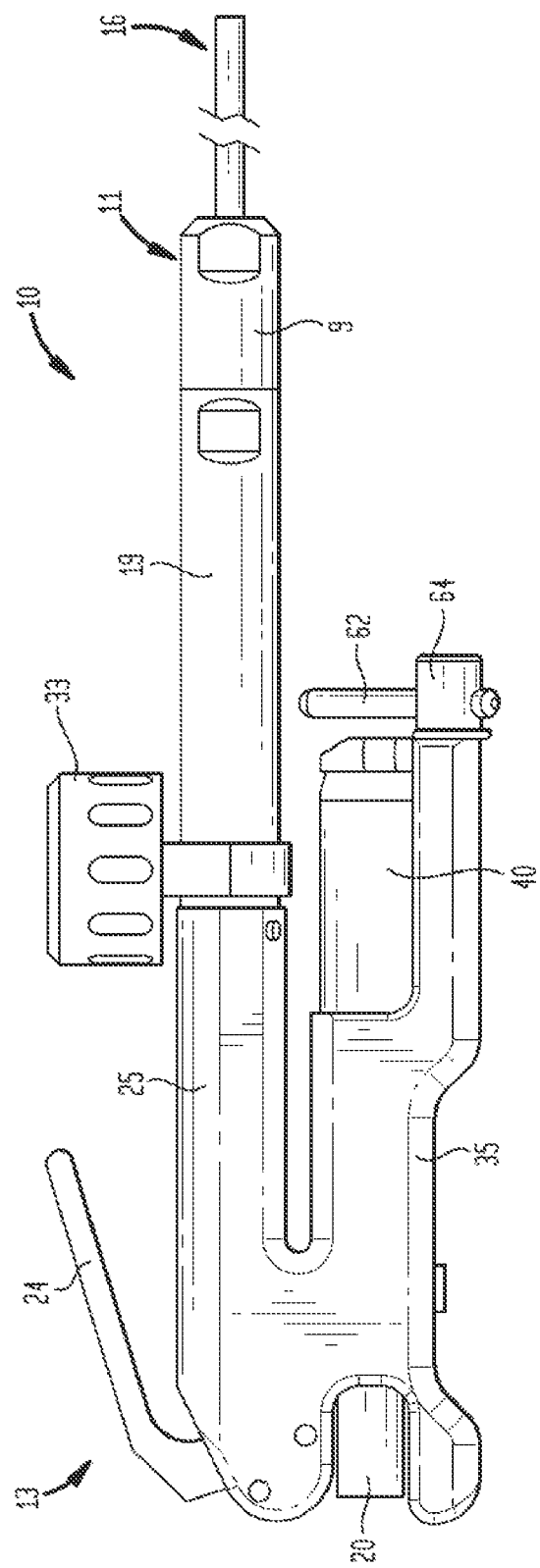

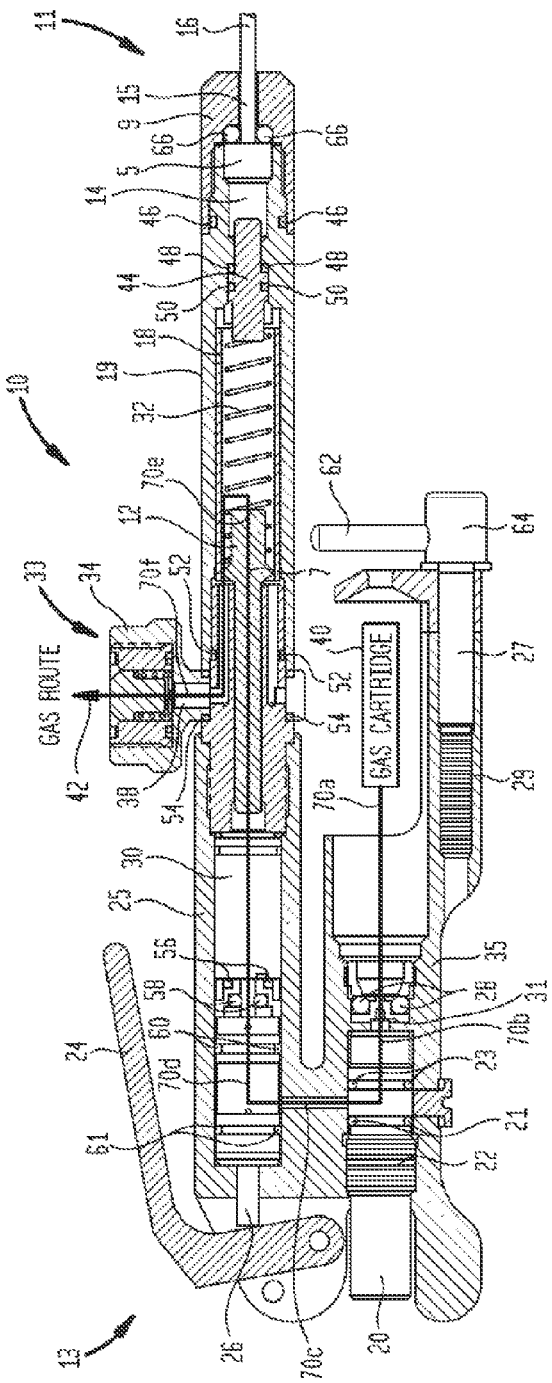

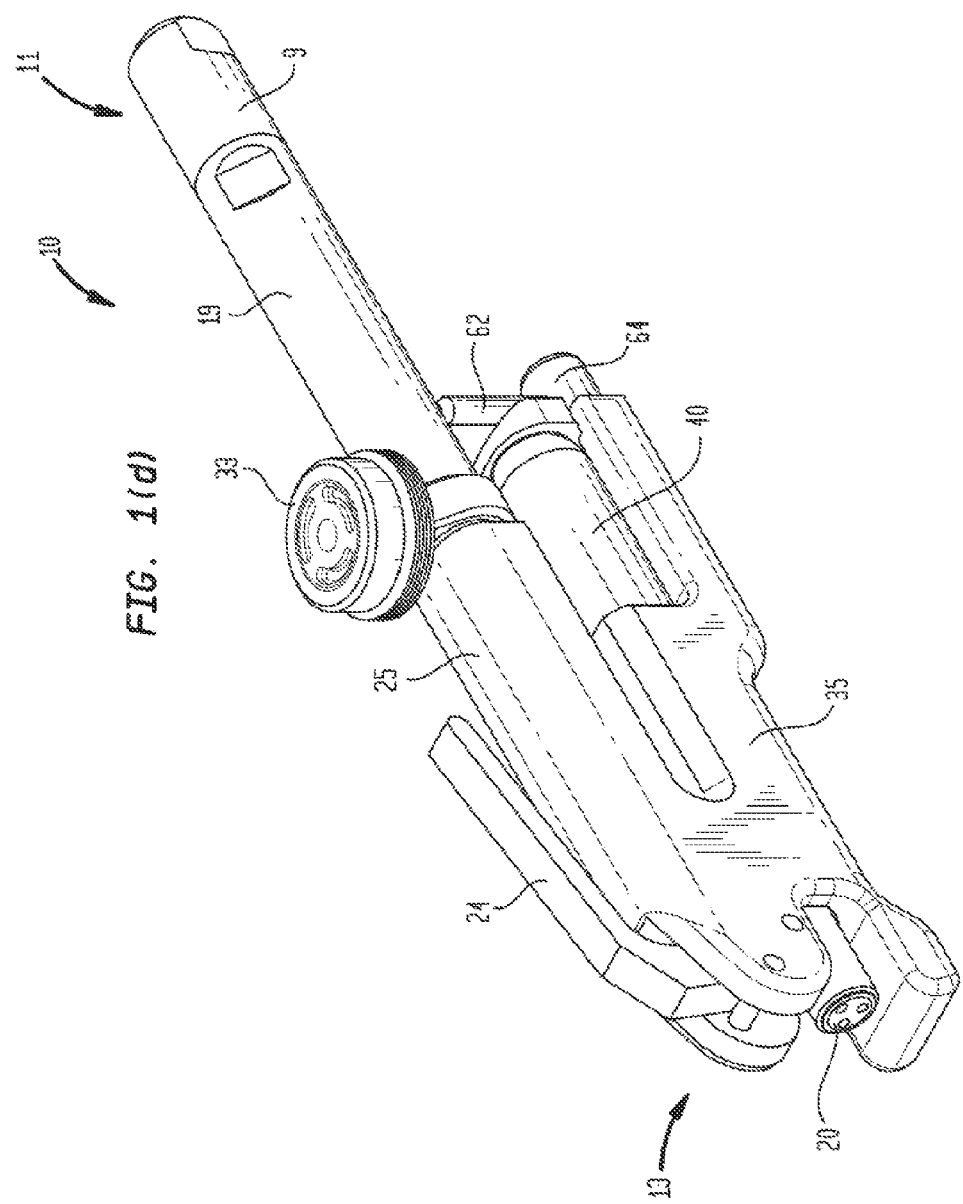

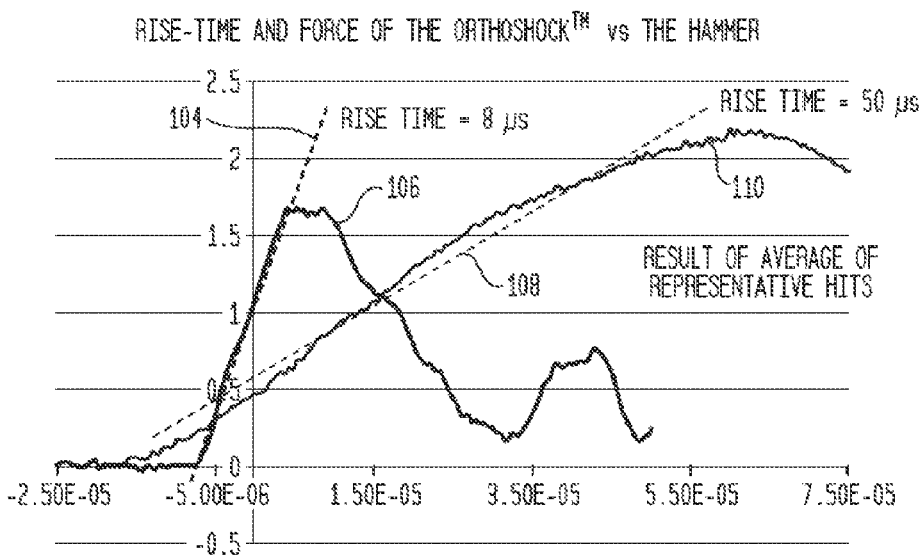
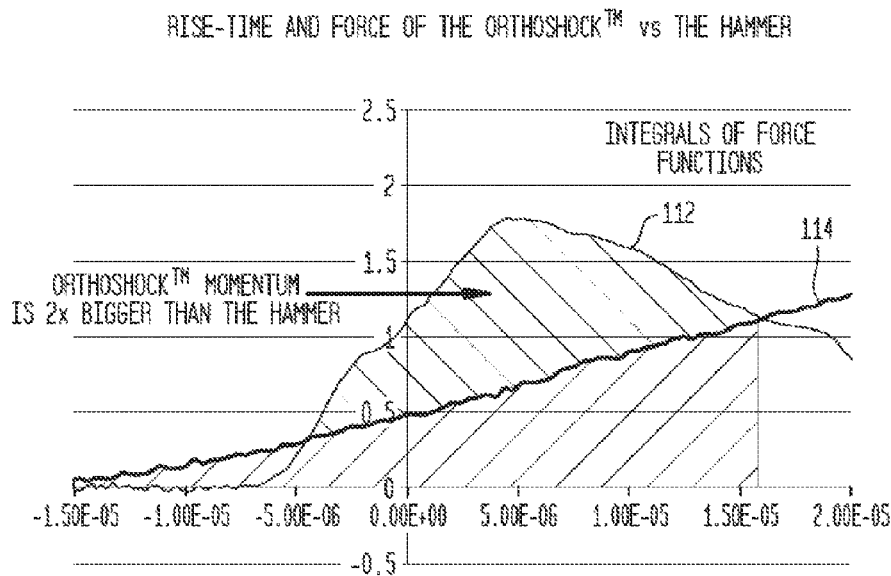

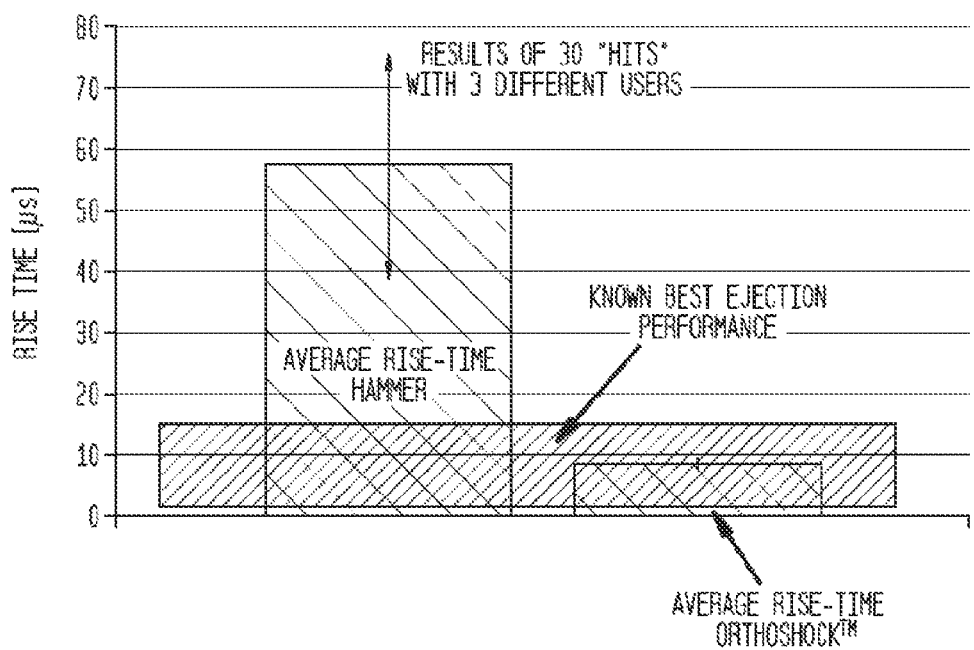

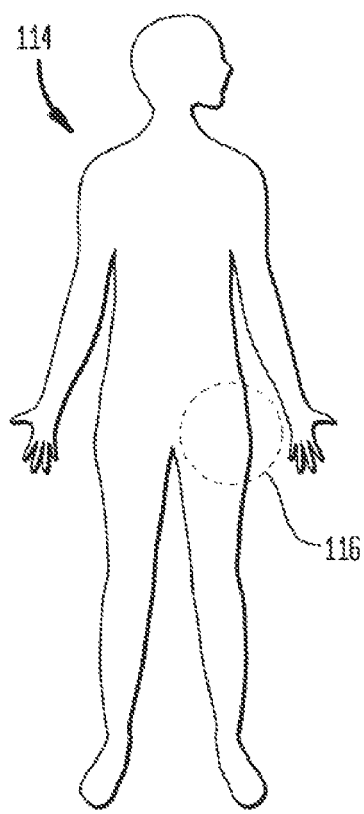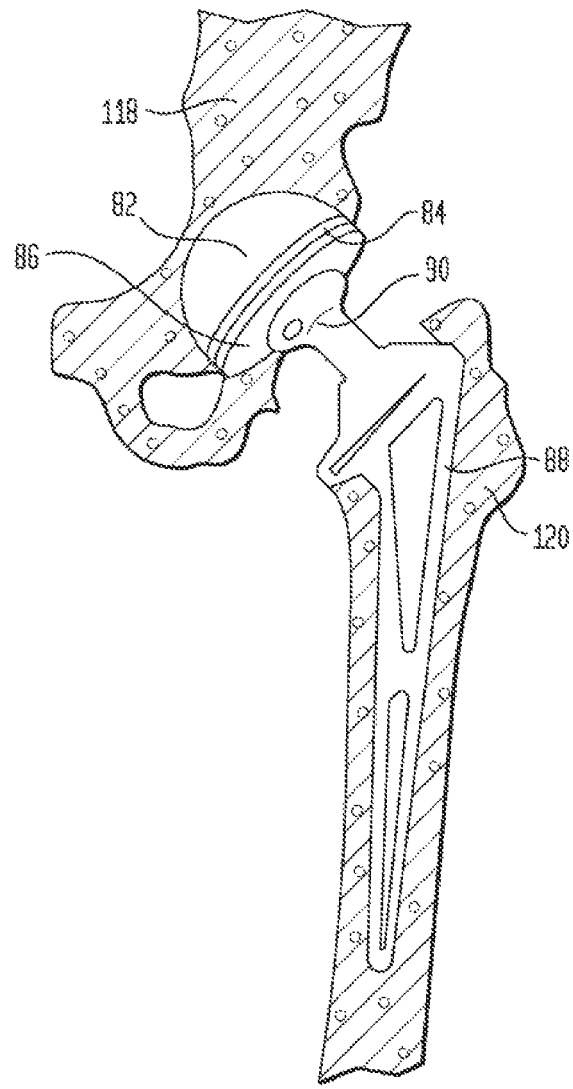

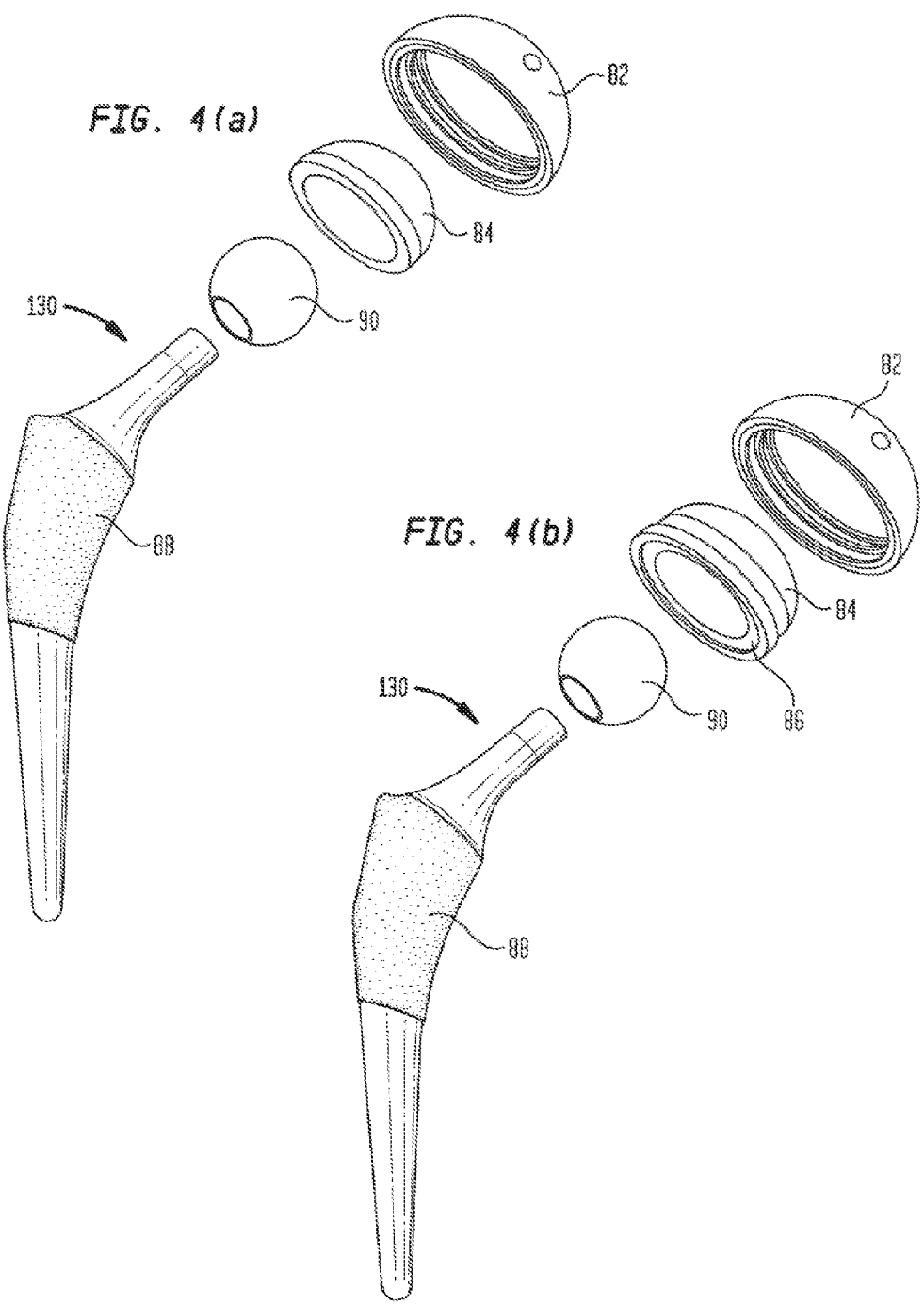

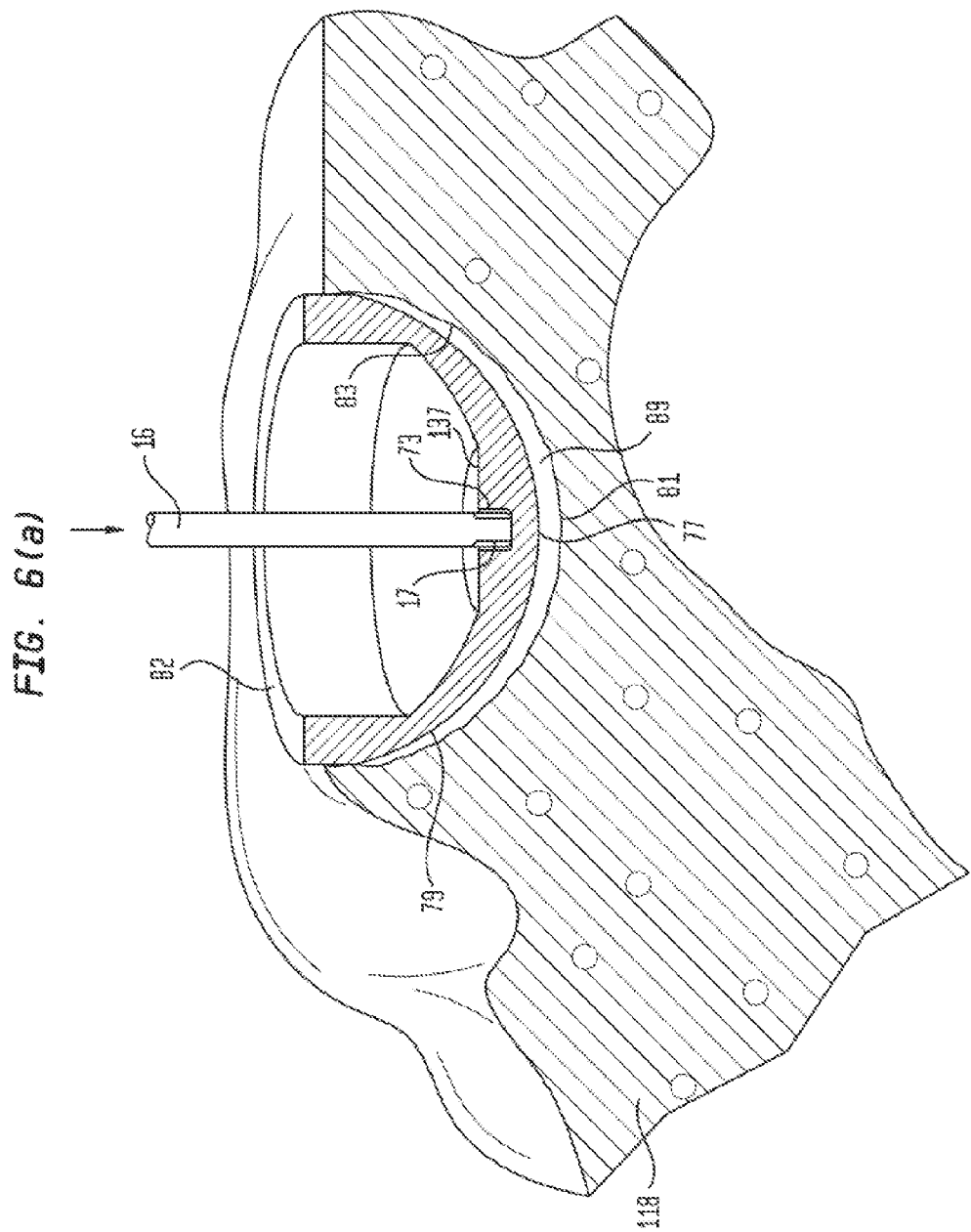

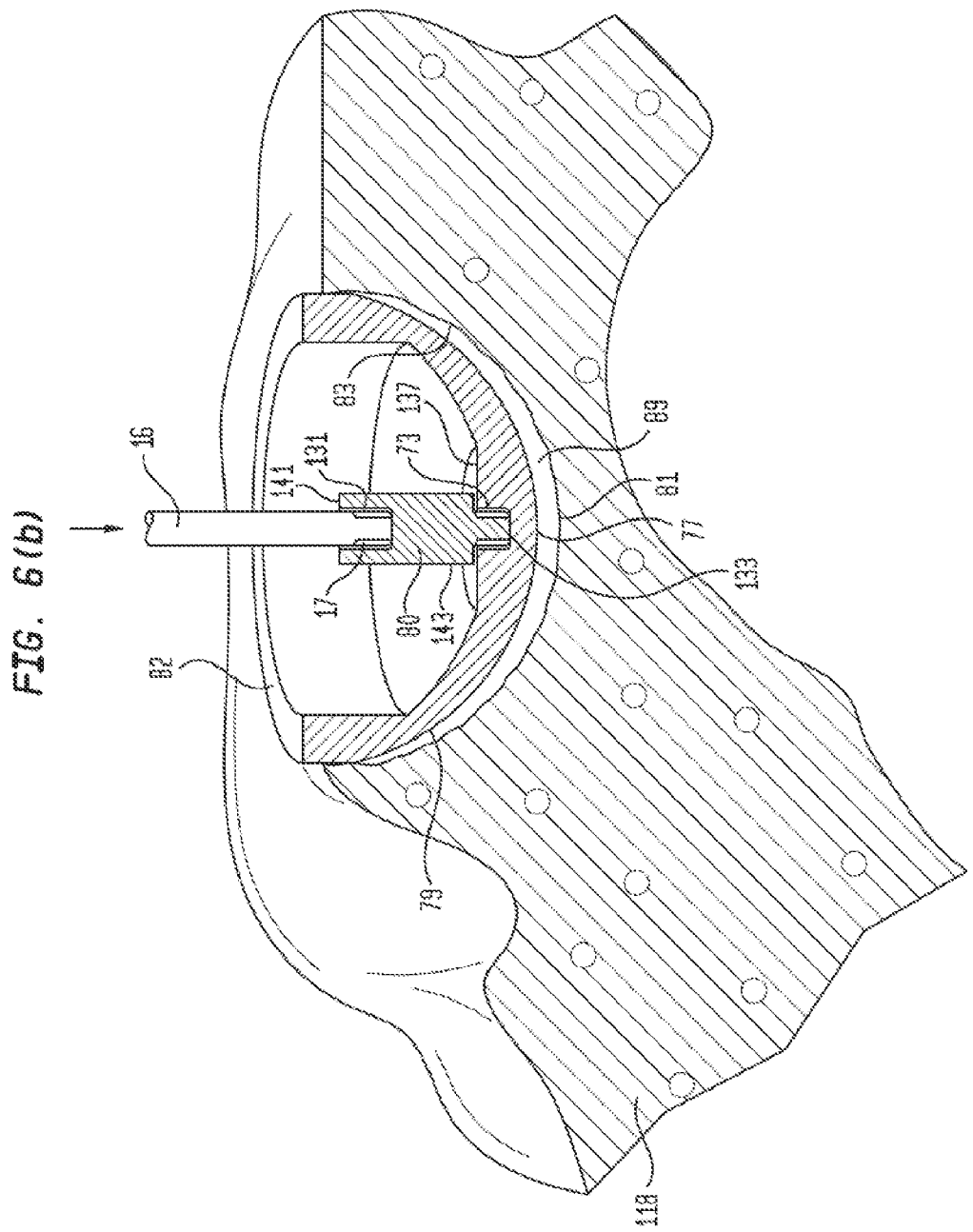

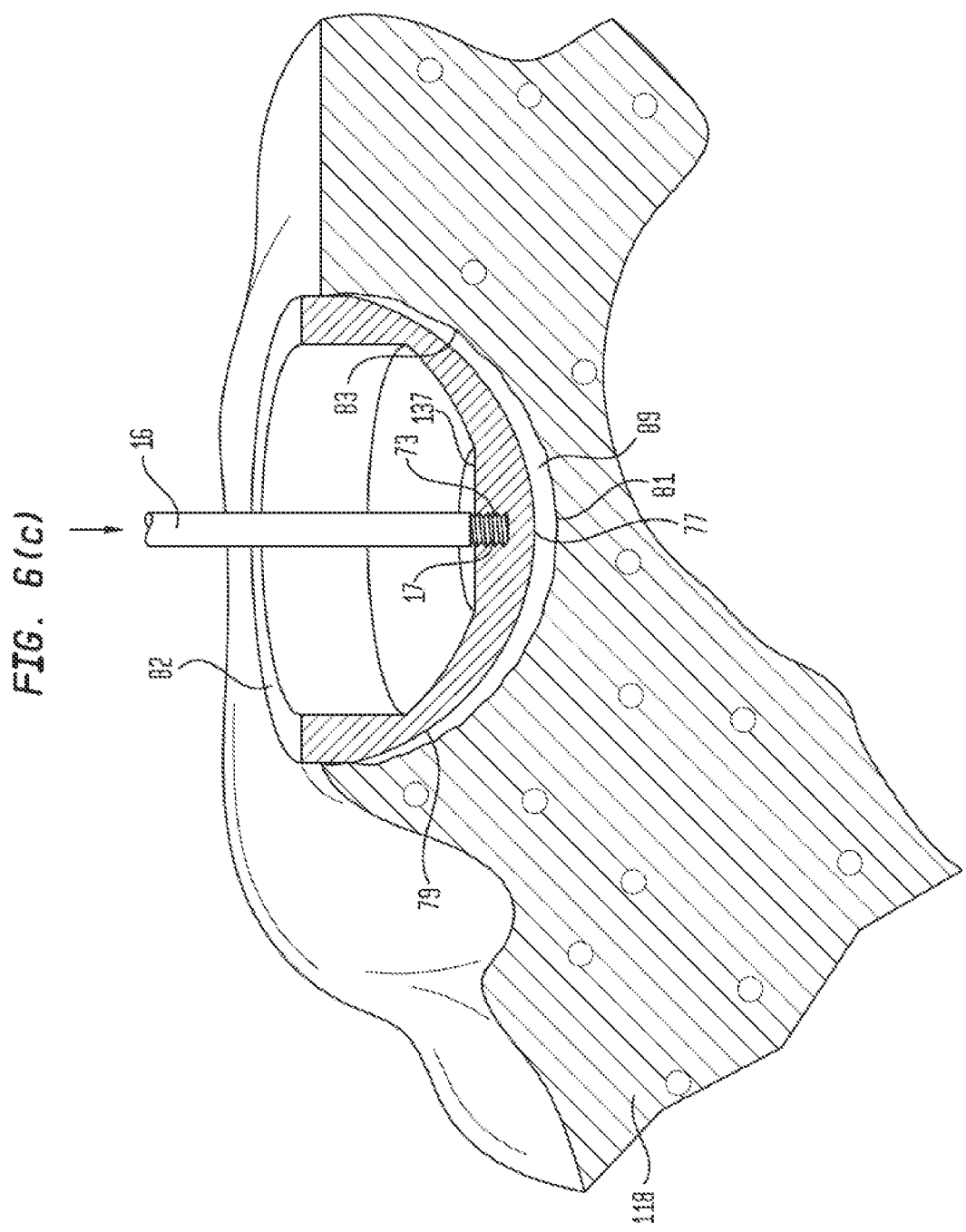

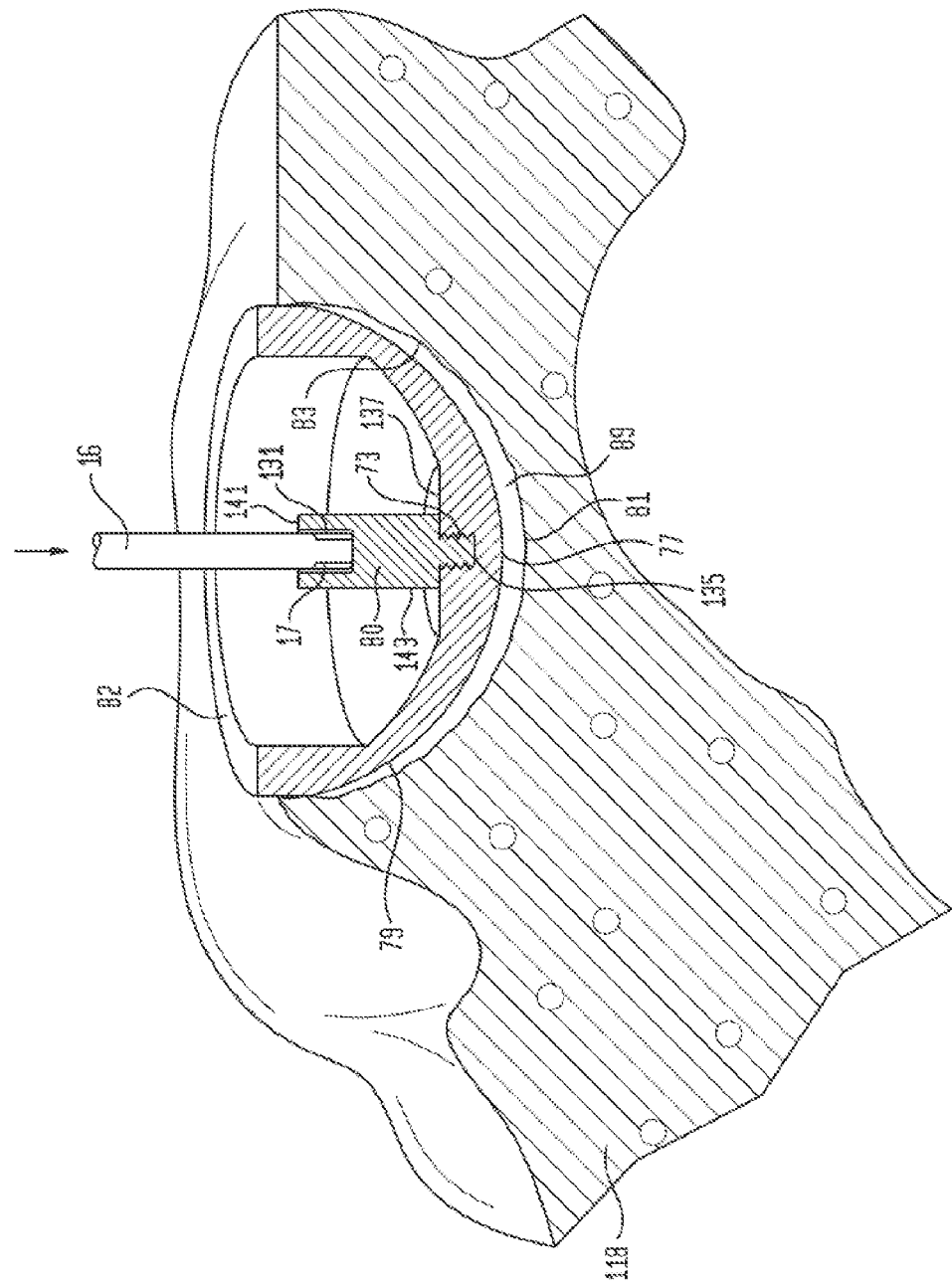

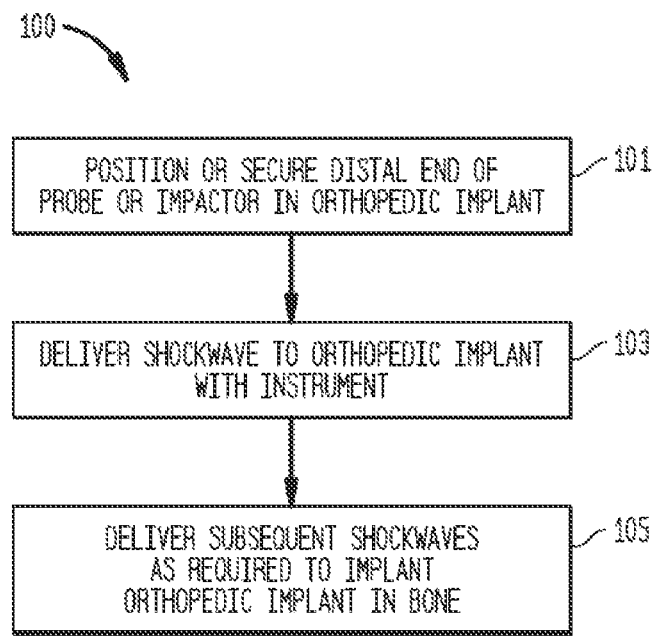

PNEUMATIC SURGICAL INSTRUMENT AND CORRESPONDING METHODS FOR IMPLANTING ORTHOPEDIC IMPLANTS IN BONE

RELATED APPLICATIONS

This application is a continuation in part and claims priority and other benefits from each of: (1) U.S. patent application Ser. No. 13/413,551 entitled "Pneumatic Surgical Instrument and Corresponding Methods for Implanting, Extracting and Reorienting Orthopedic Implants" to Mani et al. filed Mar. 6, 2012 (hereafter "the '551 patent application"); and (2) U.S. patent application Ser. No. 13/413,455 entitled "Pneumatic Surgical Instrument and Corresponding Methods for Penetrating, Resecting and Microfracturing Bone" to Mani et al. filed Mar. 6, 2012 (hereafter "the '4551 patent application"). This application also claims priority and other benefits from: (3) U.S. Provisional Patent Application Ser. No. 61/596,193 entitled "Pneumatic Surgical Instrument Configured to Deliver Shock Wave Having Fast Rise Time and Increased Energy" to Mani et al. filed Feb. 7, 2012. Each of the patent applications is hereby incorporated herein, each in its respective entirety.

FIELD OF THE INVENTION

Various embodiments of the invention described herein relate to the field of surgical instrumentation, and more particularly to components, devices, systems and methods associated with a pneumatic surgical instrument configured to deliver accurate focused impact forces to selected portions of orthopedic implant devices and drive and/or implant same into bone.

BACKGROUND

Various problems can occur when surgically implanting, removing, modifying and/or adjusting orthopedic implants in human beings. When engaging in such surgical procedures, it is necessary that physicians sometimes employ hammers to provide impulse forces to selected portions of orthopedic implants. For example, during the installation, extraction, or reorientation or adjustment of portions of an artificial hip or shoulder joint, a hammer may be employed to lock a portion of the joint in place, to move, adjust the position of or reorient a portion of the joint, or to remove or extract a portion of the joint. It is well known that artificial orthopedic hip and shoulder joints or implants can be difficult to install, extract or reorient. The delivery of impulse forces by means of a hammer to orthopedic implants is also known to have several problems, including: (a) a variable amount of force being delivered with each hammer blow; (b) an inability to finely gauge or control the amount of force that is delivered by a hammer; (c) different physicians applying different amounts of force with a hammer; (d) locational inaccuracy with respect to where hammer blows actually fall, and (e) other factors not specifically enumerated here but that are known to those skilled in the art.

What is needed is a surgical instrument that eases the installation of artificial hip, shoulder or other types of artificial joints or joint components into human bone.

SUMMARY

In one embodiment, there is provided a pneumatic surgical instrument, comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, wherein the probe has a distal end configured and shaped to engage or to be secured in or on a probe engagement feature disposed: (a) in or an orthopedic implant; or (b) in or on an orthopedic implant impactor configured to matingly engage the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and thence into the orthopedic implant or into the orthopedic impactor and the orthopedic implant, the surgical instrument being configured to drive the orthopedic implant at least partially into a void or hole formed in a patient's bone, the instrument being configured such that the shockwave delivered by the probe is substantially repeatable when the trigger is thereafter actuated by the user such that the instrument is configured to cause the orthopedic implant to engage at least portions of the void or hole in the bone.

In another embodiment, there is provided an orthopedic implant configured for use with a pneumatic surgical instrument comprising pneumatic surgical instrument comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, the probe having a distal end configured and shaped to engage or to be secured in or on a probe engagement feature disposed: (a) in or an orthopedic implant; or (b) in or on an orthopedic implant impactor configured to matingly engage the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and thence into the orthopedic implant or into the orthopedic impactor and the orthopedic implant, the surgical instrument being configured to drive the orthopedic implant at least partially into a void or hole formed in a patient's bone, the instrument being configured such that the shockwave delivered by the probe is substantially repeatable when the trigger is thereafter actuated by the user such that the instrument is configured to cause the orthopedic implant to engage at least portions of the void or hole in the bone, wherein the orthopedic implant comprises the probe engagement feature.

In yet another embodiment, there is provided an orthopedic implant system, comprising an orthopedic implant, a pneumatic surgical instrument comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, the probe having a distal end configured and shaped to engage or to be secured in or on a probe engagement feature disposed: (a) in or the orthopedic implant; or (b) in or on an orthopedic implant impactor configured to matingly engage the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and thence into the orthopedic implant or into the orthopedic impactor and the orthopedic implant, the surgical instrument being configured to drive the orthopedic implant at least partially into a void or hole formed in a patient's bone, the instrument being configured such that the shockwave delivered by the probe is substantially repeatable when the trigger is thereafter actuated by the user such that the instrument is configured to cause the orthopedic implant to engage at least portions of the void or hole in the bone.

In still another embodiment, there is provided method of generating and delivering a shockwave to an orthopedic implant with a pneumatic surgical instrument comprising a striker, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, the probe having a distal end configured and shaped to engage or to be secured in or on a probe engagement feature disposed: (a) in or the orthopedic implant; or (b) in or on an orthopedic implant impactor configured to matingly engage the orthopedic implant, the instrument being configured to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and thence into the orthopedic implant or into the orthopedic impactor and the orthopedic implant, the surgical instrument being configured to drive the orthopedic implant at least partially into a void or hole formed in a patient's bone, the instrument being configured such that the shockwave delivered by the probe is substantially repeatable when the trigger is thereafter actuated by the user such that the instrument is configured to cause the orthopedic implant to engage at least portions of the void or hole in the bone, the method comprising positioning the distal end of the probe or of the impactor in contact with the probe engagement feature of the orthopedic implant, and actuating the trigger mechanism to deliver the shockwave to the probe and thence to the orthopedic implant.

In yet a further embodiment, there is provided a method of removing a screw securing a bone plate to bone comprising generating and delivering a shockwave to the screw with a pneumatic surgical instrument having a distal end, the surgical instrument comprising a striker disposed within a longitudinal striker sleeve of the instrument, a removable probe mountable on a distal end of the instrument, a pressure regulator operably connectable to a gas cartridge mountable on or in the instrument, and a trigger mechanism comprising a trigger, the trigger mechanism being operably connected to the pressure regulator and to the striker, the probe having a distal end configured and shaped to engage a top portion of the screw, the instrument being configured to deliver at least one shock wave to the screw when the trigger is actuated by a user and a predetermined volume of gas stored at a predetermined range of pressures in the instrument is released thereby to cause the striker to move towards a distal end of the instrument and deliver the shock wave to the top portion of the screw, positioning the distal end of the probe in contact with at least a portion of the top portion of the screw, and actuating the trigger mechanism to deliver the shockwave to the screw thereby to loosen the screw from the bone and the bone plate.

Further embodiments are disclosed herein or will become apparent to those skilled in the art after having read and understood the specification and drawings hereof.

BRIEF DESCRIPTION OF THE DRAWINGS

Different aspects of the various embodiments will become apparent from the following specification, drawings and claims in which:

FIG. 1(a) shows a side view according to one embodiment of pneumatic surgical instrument 10;

FIG. 1(b) shows a cross-sectional view according to one embodiment of pneumatic surgical instrument 10;

FIG. 1(c) shows a side view according to one embodiment of probe 16;

FIG. 1(d) shows a top rear perspective view according to one embodiment of pneumatic surgical instrument 10;

FIGS. 2(a) through 2(e) show various characteristics of the rise times and forces of the shock waves generated by a commercial embodiment of instrument 10 of FIGS. 1(a) through 1(c);

FIG. 3(a) shows a representative view of patient 114 having an artificial hip assembly implanted therein at hip site 116;

FIG. 3(b) shows an artificial hip assembly comprising stem 88 implanted in femur 120, cup or socket 82 implanted in pelvis 118, liner 86 implanted conformably within insert 84, and insert 84 implanted conformably in insert 84;

FIGS. 4(a) and 4(b) show two different embodiments of components of an artificial hip assembly;

FIG. 6(a) shows one embodiment of an orthopedic implant or socket 82 being implanted in hole or void 89 in bone or pelvis 1116 by means of surgical instrument 10 and corresponding probe 16;

FIG. 6(b) shows one embodiment of an orthopedic implant or socket 82 being implanted in hole or void 89 in bone or pelvis 1116 by means of surgical instrument 10 and corresponding probe 16 and one embodiment of orthopedic impactor 80;

FIG. 6(c) shows another embodiment of an orthopedic implant or socket 82 being implanted in hole or void 89 in bone or pelvis 1116 by means of surgical instrument 10 and corresponding probe 16;

FIG. 6(d) shows the other embodiment of an orthopedic implant or socket 82 being implanted in hole or void 89 in bone or pelvis 1116 by means of surgical instrument 10 and corresponding probe 16 and another embodiment of orthopedic impactor 80;

FIG. 8 shows one embodiment of a method 100 for implanting an orthopedic implant into bone with instrument 10.

The drawings are not necessarily to scale. Like numbers refer to like parts or steps throughout the drawings.

DETAILED DESCRIPTIONS OF SOME EMBODIMENTS

Figure 2C:
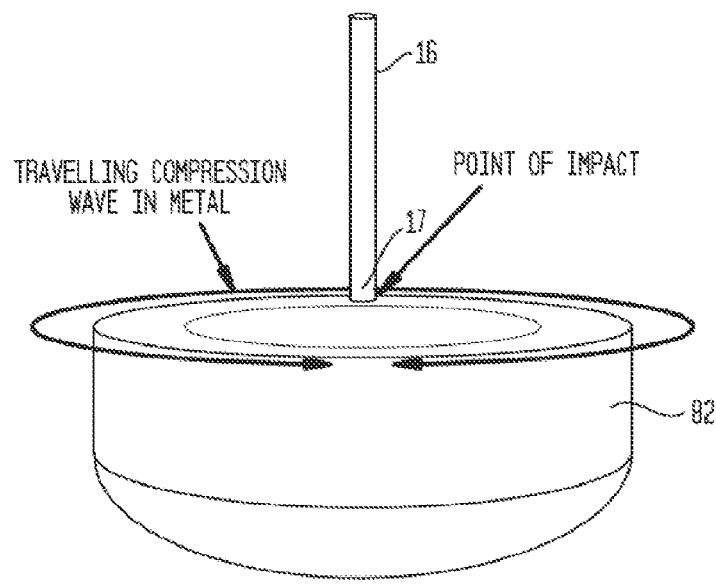

Referring now to FIGS. 1(a), 1(b) and 1(d), there are shown side, cross-sectional and top rear perspective views according to one embodiment of pneumatic surgical instrument 10, a commercial embodiment of which is known by the name OrthoShock™ and manufactured by OrthoWin™ of Gland, Switzerland. As shown in FIGS. 1(a), 1(b), 1(c) and 1(d), pneumatic surgical instrument 10 comprises striker 12, which in one embodiment is a piston. Removable probe or shockwave transfer device 16 is mountable on distal end 11 of instrument 10. Pressure regulator 20 is operably connectable to gas cartridge 40, which is mountable on or in instrument 10. According to one embodiment, gas cartridge 40 is a medical-grade $CO_2$ cartridge. Further according to one embodiment, trigger mechanism 30 comprises trigger or trigger handle 24, and trigger mechanism 30 is operably connected to pressure regulator 20 and striker 12. According to one embodiment, instrument 10 includes front metal housing 19, rear top metal housing 25, and rear bottom housing 35.

FIG. 1(c) shows a side view according to one embodiment of probe 16, where O-ring 66 is pre-mounted on proximal end 15 of the shaft projecting towards distal end 17 from a distal surface of proximal probe terminus 5. According to various embodiments, and as discussed in further detail below, the thickness, mechanical properties or materials, stiffness, or other properties of O-ring 66 may be selected to provide a desired amount of displacement or other desired performance characteristics when surgical instrument 10 is triggered or actuated. In addition, instrument 10 may be configured to receive more than one O-ring 66 between proximal terminus 5 and probe cap 9.

Continuing to refer to FIGS. 1(a) through 1(d), probe 12 has distal end 17 configured and shaped to engage: (a) at least a portion of a surface of an orthopedic implant 82, 84, 88, 90, 122, 124, or 126 (see, for example, FIG. 2(c) herein), (b) a device such as a punch configured to be placed between the orthopedic implant and the distal end of the probe (not shown in the Figures), or (c) an orthopedic implant impactor 80 configured to receive distal end 17 of probe 16 therein or thereon (see, for example, FIGS. 3(a) through 5(b) herein).

According to some embodiments, impactor 80 is configured and shaped to engage at least a portion of the surface of an orthopedic implant. Instrument 10 is configured to deliver at least one shock wave to probe 16 when trigger 24 is actuated by a user and a predetermined volume of gas stored at a predetermined range of pressures in instrument 10 is released thereby to cause striker 12 to move towards distal end 11 of instrument 10 and deliver the shock wave to proximal end 15 of probe 16.

The shockwave delivered by instrument 10 and probe 16 is substantially repeatable by instrument 10 when trigger 24 is actuated again by the user for the delivery of a subsequent shockwave by instrument 10 after the volume of gas exhausted by instrument 10 through gas exhaust device 33 has been replenished within instrument 10 from gas cartridge 40 through gas regulator 20.

According to one embodiment, the predetermined volume of gas stored at a predetermined range of pressures is contained in a chamber disposed within trigger mechanism 30, and is released to force the striker towards distal end 11 of instrument 10 when trigger mechanism 30 is actuated by the user by means of trigger handle 24 and actuator 26. Other means of triggering trigger mechanism 30 are contemplated, such as solenoids, mechanically depressible buttons, and so on. Moreover, the chamber containing the predetermined volume of gas stored at a predetermined range of pressures in instrument 10 may be housed elsewhere in instrument 10 other than as part of trigger mechanism 30, such as, by way of example, in a chamber disposed in or attached to pressure regulator 20, or in another location within or on instrument 10. Note that in the embodiment of instrument 10 shown in FIGS. 1(a), 1(b) and 1(c), striker 12 is disposed within longitudinal striker sleeve 18, although other embodiments are contemplated.

Further according to various embodiments, pneumatic instrument 10 may be configured such that the shockwave provided by probe 16 has a rise time ranging between about 2 microseconds and about 20 microseconds, between about 4 microseconds and about 16 microseconds, or between about 6 microseconds and about 10 microseconds, and that instrument 10 may further be configured to cause the shock wave delivered by probe 16 to an orthopedic implant to travel from a first side of the orthopedic implant to a second opposing side of the orthopedic implant is less than about 30 microseconds, or less than about 20 microseconds, more about which is said below. Other rise times are also contemplated.

Referring still to FIGS. 1(a) through 1(d), and according to one embodiment, instrument 10 comprises removable probe cap 9, which is configured to receive proximal end 15 of probe 16 therein or therethrough, where probe cap 9 is mountable on distal end 11 of instrument 10, and where proximal probe terminus 5 is located proximally within instrument 10 behind probe cap 9. Firing pin 44 is disposed between a distal end of striker 12 and a proximal end of firing pin receiver 14. The distal end of striker 12 is configured to engage and strike a proximal end of firing pin 44 and drive same towards firing pin receiver 14, which is configured to receive the distal end of firing pin 44 therein and transfer the shockwave delivered thereby to proximal probe terminus 5.

As further shown in FIG. 1(c), probe O-ring 66 is disposed near proximal end 15 of probe 16 between an inner surface of probe cap 9 and a distal portion of probe terminus 5. In one embodiment, probe O-ring 66 comprises nitrile and has a thickness ranging between about 2 mm and about 3 mm, although other ranges of the thickness of O-ring 66 are contemplated, such as between about 1 mm and about 6 mm, between about 1.5 mm and about 5 mm, between about 2 mm and about 4 mm. In one embodiment, O-ring 66 has an inner diameter of about 2.8 mm, an outer diameter of about 7 mm, and a thickness of 2.64 mm. According to one embodiment, probe 16 is displaced by about 0.5 mm when instrument 10 is actuated. Other amounts of the displacement of probe 16 when instrument 10 is triggered or actuated may be provided, however, such as displacement of about 0.2 mm, about 0.4 mm, about 0.6 mm, about 0.8 mm, and about 1 mm.

In conjunction with the amount of force provided by the distal end of striker 12 to firing pin 44, firing pin receiver 14, and probe terminus 5, the number, thickness or other properties of O-rings 66 may be configured to provide a desired amount of displacement of probe 16, or a desired force or energy signature, when instrument 10 is triggered. Further according to some embodiments, other O-rings 46, 48, 50, 52, 54, 56, 58, 60, 61, 21, 23 and 28 in instrument 10 may also comprise nitrile, which does not absorb $CO_2$ gas and thus prevents the degradation or expansion of such O-rings caused by exposure to $CO_2$ gas.

Still referring to FIG. 1(b), and according to one embodiment, pressure regulator 20 includes a pin 31 that is configured to puncture gas cartridge 40 when replaceable gas cartridge 40 is mounted in or on instrument 10. Gas cartridge 40 may be inserted or removed form instrument 10 by turning gas cartridge replacement and removal mechanism handle 62, and corresponding shaft end 64, rod 27, and threaded portion 29 inwardly or outwardly, as the case may be. Pressure regulator 20 directs and regulates the pressure of gas originating in cartridge 40 to trigger mechanism 30, and includes spring 22, which is configured to push a valve located in pressure regulator 20 closed after a predetermined amount or volume of gas has been emitted from cartridge 40 into pressure regulator 20 and trigger mechanism 30. According to some embodiments, gas regulator 20 is configured to provide pressurized gas to trigger mechanism 30 at pressures ranging between about 15 bars and about 60 bars, or between about 25 bars and about 35 bars. A nominal regulated pressure of 29 bars is preferred according to one embodiment.

Continuing to refer to FIG. 1(b), there are shown interconnected gas passageways 70a, 70b, 70c, 70d, 70e, and 70f, which are routed, respectively, through gas cartridge 40, gas regulator 20, between gas regulator 20 and trigger mechanism 30, trigger mechanism 30, striker 12 (through central aperture 7), and around the top portion of striker 12. Gas travelling through such passageways is ultimately exhausted through gas exhaust device 33 as exhaust gas 42. According to one embodiment, and as shown in FIG. 1(b), gas exhaust device 33 comprises gas exhaust filter housing 34, a replaceable gas exhaust filter cartridge (not shown in the drawings), and gas exhaust filter valve 38. Gas exhaust device 33 is configured to trap particulate contaminants in the replaceable gas exhaust filter cartridge that may be present in gas provided by gas cartridge 40, and prevent contamination of the sterile field during a surgical procedure.

Referring to FIGS. 1(a) through 1(d), and according to one embodiment, probe 16 comprises a metal or metal alloy such as stainless steel, and has a length ranging between about 10 cm and about 30 cm, and a diameter ranging between about 2.8 mm and about 3.4 mm. Other probe lengths and diameters are also contemplated. Distal end 17 of probe 16 may be configured to accept an orthopedic implant impactor 80 (see subsequent Figures) thereon or therein, and/or may be configured to engage a portion of a surface of an orthopedic implant directly.

Referring now to FIGS. 2(a) through 2(e), there are shown various characteristics of the rise times and forces of the shock waves generated by a commercial embodiment of instrument 10 of FIGS. 1(a) through 1(d) known as the OrthoShock™ surgical instrument. As illustrated in FIG. 2(a), there is shown the output signal (or shockwave or impulse force) delivered according to one embodiment of the OrthoShock surgical instrument disclosed and described herein. The shockwave or impulse force output signal delivered by an OrthoShock™ surgical instrument to an orthopedic implant or device is juxtaposed with the output signals provided by a conventional orthopedic hammer. As will be seen by referring to FIG. 2(a), the rise time, or the amount of time over which the shockwave or impulse force is provided by instrument 10 is much shorter than that provided by a conventional orthopedic hammer. In the example shown in FIG. 2(a), the total rise time is about 6 microseconds, as compared to a 50 microsecond rise time characteristic of a hammer employed for the same purpose. The steeper the curve of the output signal, the better the initial impulse. Further as shown in FIG. 2(a), the rise time of the OrthoShock™ surgical instrument is about five times greater than that of a corresponding orthopedic hammer.

FIG. 2(b) shows a comparison of integrated output shockwave or impulse force output signals provided by one embodiment of the surgical instrument described and disclosed herein relative to those provided by a hammer, and corresponds to the results shown in FIG. 2(a). The greater the integral, especially during the first 20 microseconds in the context of delivering shockwave to an artificial hip implant insert for the purpose of ejecting same, the bigger the change in momentum, and the more energy that is usefully transferred to the orthopedic implant or device to cause its ejection from an artificial hip socket. This means that use of surgical instrument 10 disclosed and described herein results in particularly efficacious and easy removal, reorientation or insertion of an artificial hip implant insert with respect to an artificial hip implant socket.

FIG. 2(c) shows one embodiment of a travelling shock- or compression wave in an orthopedic implant 82 provided by the surgical instrument described and disclosed herein. Surgical instrument 10 described and disclosed herein has been discovered to cause a shockwave to travel from one side of an orthopedic implant insert to the opposite side in about 20 microseconds.

Figure 2D:
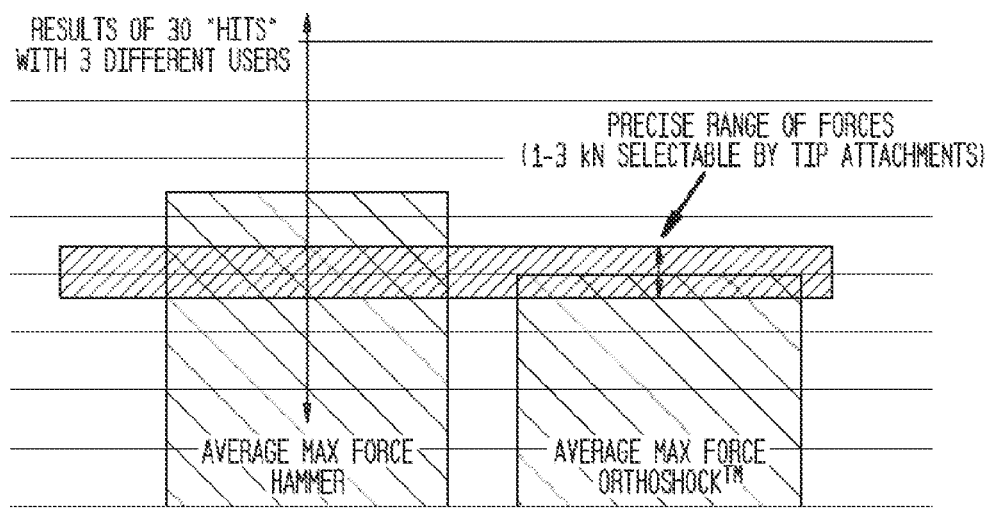
Figure 5A:
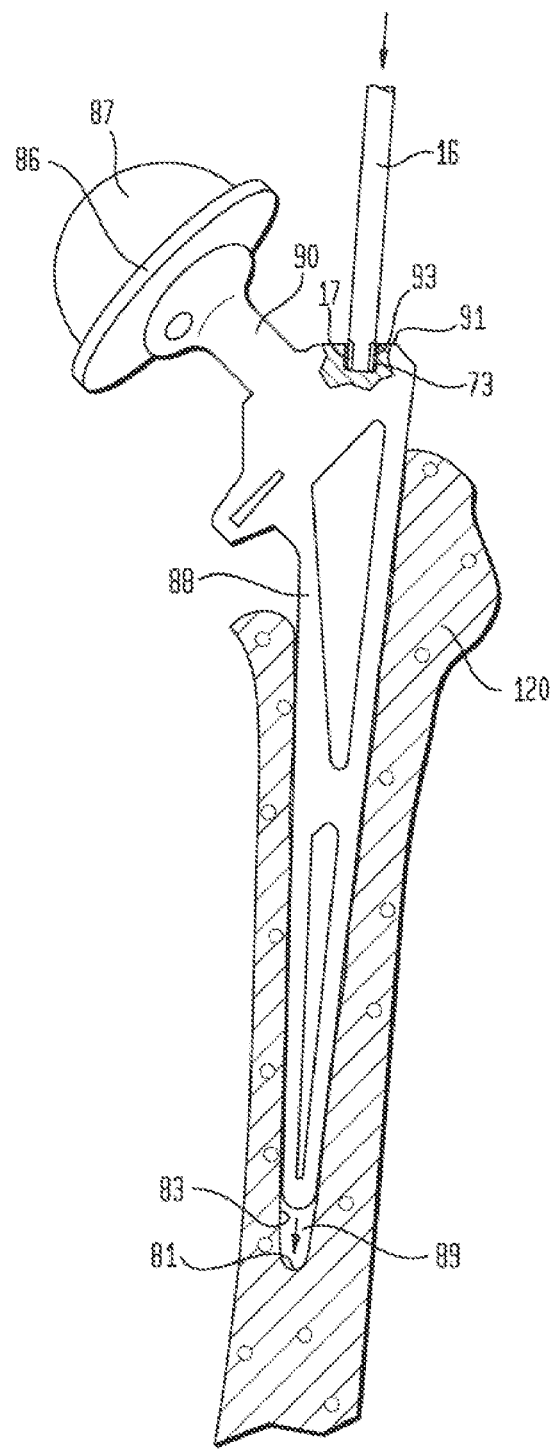
FIG. 5(a) shows one embodiment of a portion of an artificial hip assembly comprising stem 88 being implanted in hole or void 89 in bone or femur 120 by means of surgical instrument 10 and corresponding probe 16.
Figure 5B:
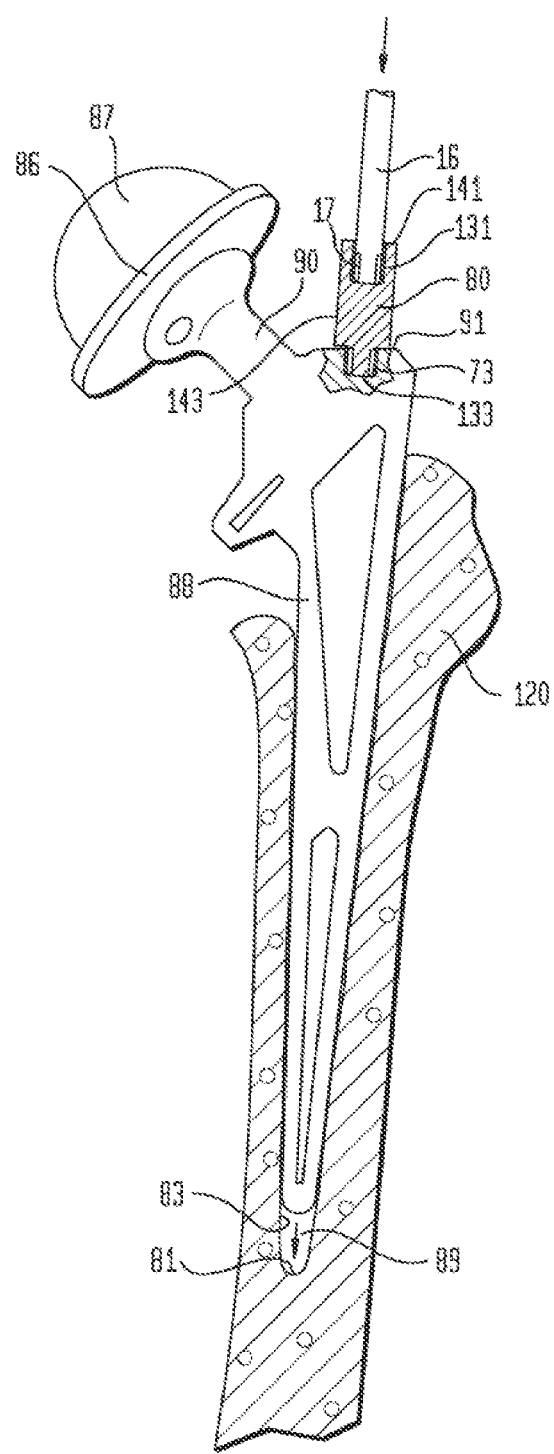
FIG. 5(b) shows one embodiment of a portion of an artificial hip assembly comprising stem 88 being implanted in hole or void 89 in bone or femur 120 by means of surgical instrument 10 and corresponding probe 16 and one embodiment of orthopedic impactor 80.
Figure 5C:
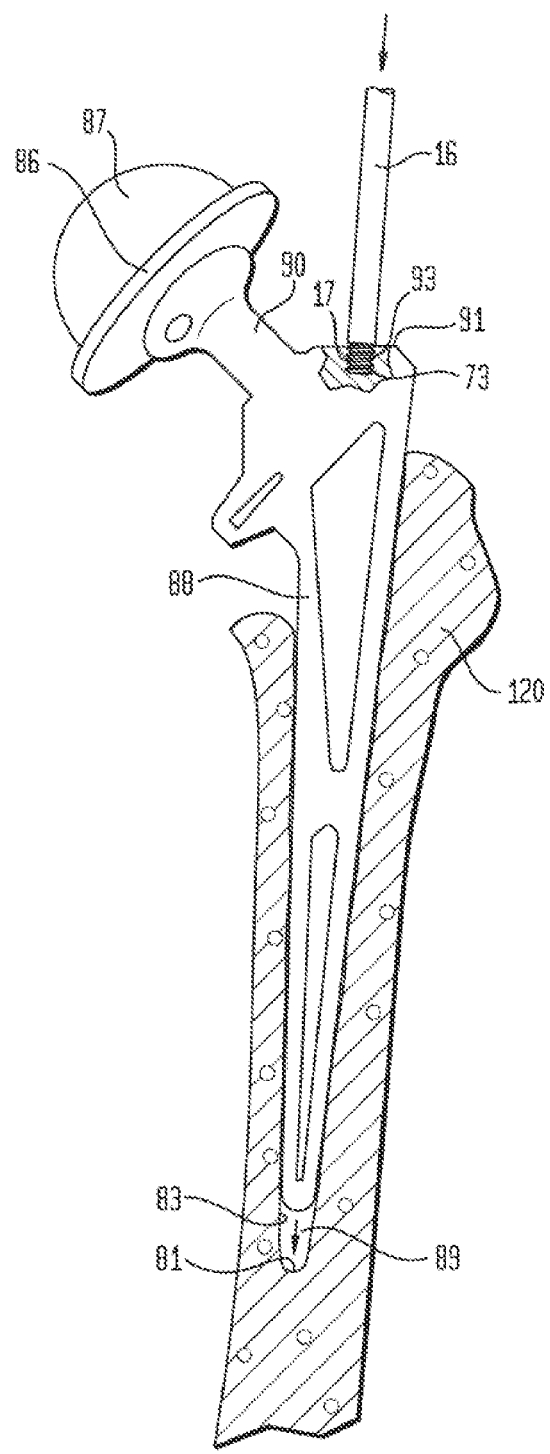
FIG. 5(c) shows another embodiment of a portion of an artificial hip assembly comprising stem 88 being implanted in hole or void 89 in bone or femur 120 by means of surgical instrument 10 and corresponding probe 16.
Figure 5D:
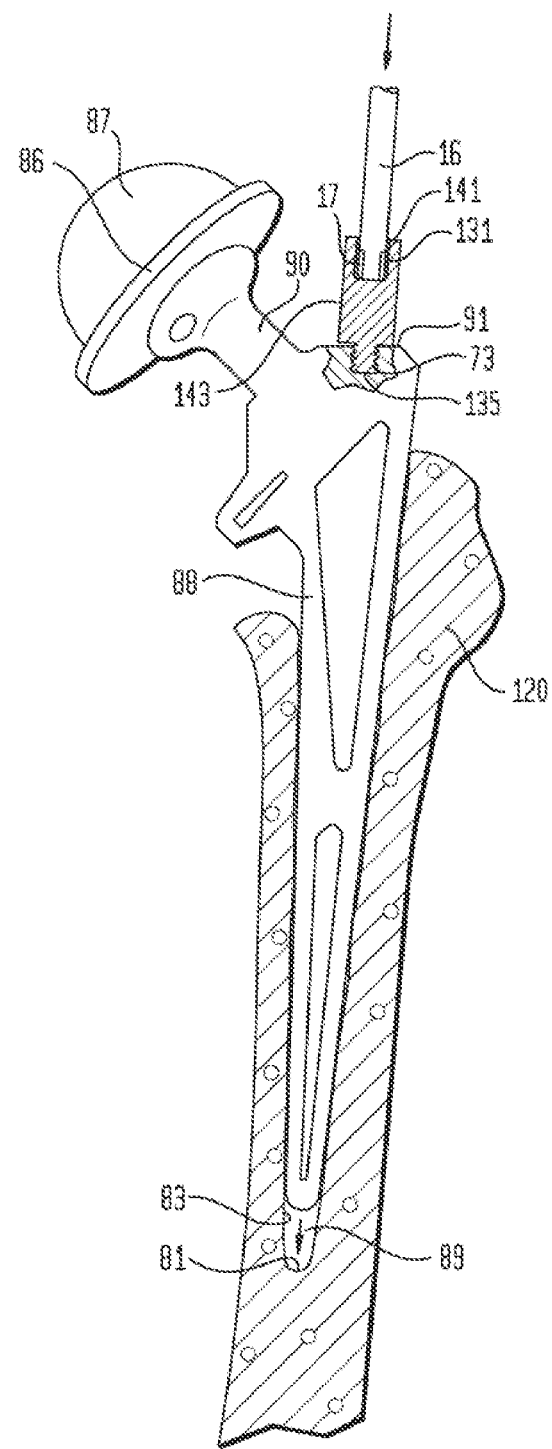
FIG. 5(d) shows the other embodiment of a portion of an artificial hip assembly comprising stem 88 being implanted in hole or void 89 in bone or femur 120 by means of surgical instrument 10 and corresponding probe 16 and another embodiment of orthopedic impactor 80.

FIGS. 2(d) and 2(e) show rise time results obtained with one embodiment of surgical instrument 10 described and disclosed herein in comparison to those obtained with a hammer. As shown in FIGS. 2(d) and 2(e), surgical instrument 10 described and disclosed herein provides much smaller rise times and improved orthopedic implant insert ejection performance relative to a conventional hammer. Repeatability and ejection performance are markedly improved.

Various embodiments of orthopedic implant impactor 80 described and shown in the '551 patent are contemplated for use in conjunction with instrument 10 for purposes of driving or implanting orthopedic implants into voids or holes formed in bone, and configured to receive the orthopedic implants therein, more about which is said below.

Figure 7A:
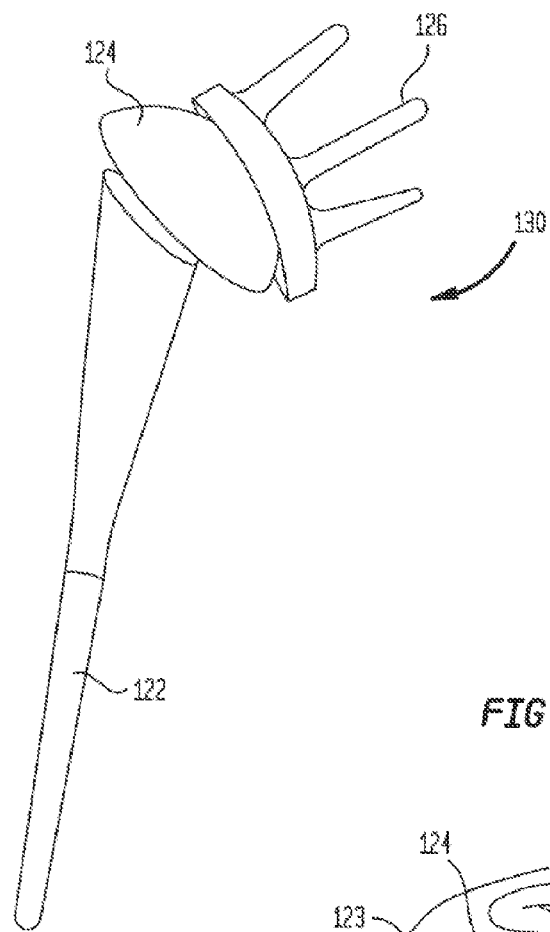
FIGS. 7(a) and 7(b) show shoulder orthopedic implant system 130 and system 130 implanted in a patient, respectively.
Figure 7B:
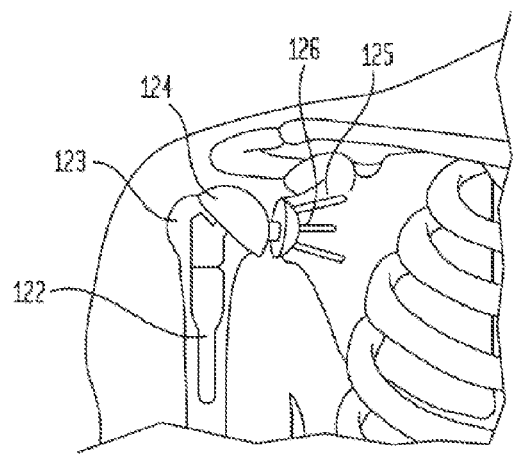

Referring now to FIG. 3(a), there is shown a representative view of patient 114 having an artificial hip assembly implanted therein at hip site 116. As shown in FIG. 6(b), the artificial hip assembly comprises stem 88 implanted in femur 120, cup or socket 82 implanted in pelvis 118, liner 86 implanted conformably within insert 84, and insert 84 implanted conformably in insert 84. The components of an artificial hip assembly according to one embodiment, namely stem 88, ball 90, insert 84, and cup or socket 82, are shown in FIG. 7(a). The components of an artificial hip assembly according to another embodiment, namely stem 88, ball 90, liner 86, insert 84, and cup or socket 82 are shown in FIG. 7(b). All of orthopedic implants or components stem 88, ball 90, liner 86, insert 84, and/or cup or socket 82 shown in FIGS. 7(a) and 7(b) may be implanted, extracted or reoriented or adjusted using surgical instrument 10 as described and shown in the above-referenced '551 patent, with or without impactor 80. In addition, surgical instrument 10, probe 16, optionally impactor 80 or another device, and the orthopedic implant that is to be implanted in a void or hole formed in bone 118 or 120 may be configured and shaped such that a predetermined number of sequentially-delivered shock waves are required to implant an orthopedic implant in a void or hole formed in bone 118 or 120.

By way of example, a plurality of strikes delivered by instrument 10 to an orthopedic implant such as stem 88 or socket 82 are typically required to insert the orthopedic implant in a void or hole 89 formed in a patient's bone, where the void or hole 89 has been formed by a surgeon using appropriate tools and techniques well known in the art such that hole or void 89 is configured to accept the orthopedic implant therein. Sufficient strikes are delivered by instrument 10, under the control of the surgeon, to cause the orthopedic implant to suitably engage the sidewalls and other portions of the surfaces forming the hole or void 89 such that the orthopedic implant will remain implanted therein and attached thereto after the implant has been driven into place using instrument 10. The orthopedic implant may be driven into void or hole 89 by instrument 10 with or without impactor 80, or with or without the aforementioned device.

Similarly, shoulder orthopedic implant system 130 shown in FIGS. 7(*a*) and 7(*b*) comprising shoulder orthopedic implant stem 122, shoulder orthopedic implant ball and socket 124, and shoulder orthopedic anchor 126 may be implanted using surgical instrument 10 described and disclosed herein, with or without impactor 80, or with or without the aforementioned device.

Referring now to FIG. 5(*a*), there is shown one embodiment of a portion of an artificial hip assembly comprising stem 88 as it is being implanted in hole or void 89 in bone or femur 120 by means of surgical instrument 10 and corresponding probe 16 and distal end 17 thereof. Void or hole 89 is first formed by a surgeon in bone or femur 120 in accordance with the techniques described above, and has dimensions suitable to receive the distal or lower end of stem 88 therein. The distal end of stem 88 is then placed in void or hole 89 until it engages at least portions of hole or void 89, such as sidewalls 83. The distal end of probe 16 is then positioned in recess or other probe engagement feature 73 formed on a proximal or other suitable surface 91 of stem 88, and the trigger of instrument 10 is actuated by the surgeon. Successive shocks thereby delivered to the proximal end of stem 88 cause stem 88 to be forced downwardly ever deeper into hole or void 89, preferably until the distal end of stem 88 engages or is in close proximity to the bottom 81 of hole or void 89, or at least until stem 88 has achieved a suitable fit or anchored position in void or hole 89. As shown in FIG. 5(*a*), distal end 17 of probe 16 is configured and shaped to engage at least a portion of a surface 91 or recess or other probe engagement feature 73 disposed in, orthopedic implant or stem 88. Note that according to other embodiments probe engagement feature 73 may be a positive feature such as a bump or protrusion extending above the surface the orthopedic implant, where probe 16 or impactor 80 is correspondingly configured to engage matingly with same.

In other embodiments, and as shown in FIG. 5(*b*) (and/or as disclosed and described in the above-referenced '551 patent), an orthopedic implant impactor 80 having proximal and distal ends 141 and 143 is configured to matingly engage with probe engagement feature 73 of stem 88 via impactor engagement feature 133. In such embodiments, instrument 10 is configured to deliver at least one shock wave to probe 16 when the trigger is actuated by a surgeon or user, and a predetermined volume of gas stored at a predetermined range of pressures in instrument 10 is released thereby to cause the striker to move towards a distal end of instrument 10 and deliver a shock wave to the proximal end of probe 16 and through impactor 80 such that the orthopedic implant or stem 88 can be driven at least partially into void or hole 89 formed in patient's bone 120. The shockwave delivered by probe 16 is substantially repeatable by instrument 10 when the trigger is thereafter actuated by the surgeon or user such that the orthopedic implant or stem 88 can engage at least portions of void or hole 89, such as sidewalls 83.

Referring now to FIG. 5(*c*), there is shown distal end 17 of probe 16 configured and shaped to engage threadably recess or probe engagement feature 73 disposed in orthopedic implant or stem 88. In other embodiments, and as shown in FIG. 5(*d*) (and/or as disclosed and described in the above-referenced '551 patent), an orthopedic implant impactor 80 having proximal and distal ends 141 and 143 is configured to matingly engage threadably with probe engagement feature 73 of stem 88 via threaded impactor engagement feature 135. In such embodiments, instrument 10 is configured to deliver at least one shock wave to probe 16 when the trigger is actuated by a surgeon or user, and a predetermined volume of gas stored at a predetermined range of pressures in instrument 10 is released thereby to cause the striker to move towards a distal end of instrument 10 and deliver a shock wave to the proximal end of probe 16 and through impactor 80 such that the orthopedic implant or stem 88 can be driven at least partially into void or hole 89 formed in patient's bone 120. The shockwave delivered by probe 16 is substantially repeatable by instrument 10 when the trigger is thereafter actuated by the surgeon or user such that the orthopedic implant or stem 88 can engage at least portions of void or hole 89, such as sidewalls 83.

Referring to FIG. 6(*a*), there is shown one embodiment of an orthopedic hip socket 82 as it is being implanted in bone hole or void 89 in bone or pelvis 118 by means of surgical instrument 10 and corresponding probe 16 and distal end 17 thereof. Bone void or hole 89 is first formed by a surgeon in bone or pelvis 118 in accordance with the well-known techniques described above, and has dimensions suitable to receive the distal or lower end 77 of socket 82 therein. Distal portions 77 of socket 82 are then placed in bone void or hole 89 until they engage at least portions of hole or void 89, such as sidewalls 83. Distal end 17 of probe 16 is then positioned in recess or other probe engagement feature 73 formed on inner lower surface 137 of socket 82, and the trigger of instrument 10 is actuated by the surgeon. Successive shocks thereby delivered to socket 82 cause socket 82 to be forced downwardly deeper into hole or void 89, preferably until the outer lower or distal portions of socket 82 engage or are in close proximity to the bottom 81 of hole or void 89, or at least until socket 82 has achieved a suitable fit or anchored position in void or hole 89. As shown in FIG. 6(*a*), distal end 17 of probe 16 is configured and shaped to engage at least a portion of inner lower surface 137 of socket 82, which in the illustrated embodiment comprises a recess or other probe engagement feature 73.

In other embodiments, and as shown in FIG. 6(*b*) (and/or as disclosed and described in the above-referenced '551 patent), an orthopedic implant impactor 80 having proximal and distal ends 141 and 143 is configured to matingly engage with probe engagement feature 73 of socket 82 via impactor engagement feature 133. In such embodiments, instrument 10 is configured to deliver at least one shock wave to probe 16 when the trigger is actuated by a surgeon or user, and a predetermined volume of gas stored at a predetermined range of pressures in instrument 10 is released thereby to cause the striker to move towards a distal end of instrument 10 and deliver a shock wave to the proximal end of probe 16 and through impactor 80 such that the orthopedic implant or socket 82 can be driven at least partially into void or hole 89 formed in patient's bone 120. The shockwave delivered by probe 16 is substantially repeatable by instrument 10 when the trigger is thereafter actuated by the surgeon or user such that the orthopedic implant or socket 82 can engage at least portions of void or hole 89, such as sidewalls 83.

Referring now to FIG. 6(c), there is shown distal end 17 of probe 16 configured and shaped to threadably engage recess or other probe engagement feature 73 having corresponding threads disposed in orthopedic implant or socket 82. In other embodiments, and as shown in FIG. 6(d) (and/or as disclosed and described in the above-referenced '551 patent), an orthopedic implant impactor 80 having proximal and distal ends 141 and 143 is configured to matingly engage threadably with probe engagement feature 73 of socket 82 via threaded impactor engagement feature 135. In such embodiments, instrument 10 is configured to deliver at least one shock wave to probe 16 when the trigger is actuated by a surgeon or user, and a predetermined volume of gas stored at a predetermined range of pressures in instrument 10 is released thereby to cause the striker to move towards a distal end of instrument 10 and deliver a shock wave to the proximal end of probe 16 and through impactor 80 such that the orthopedic implant or stem 88 can be driven at least partially into void or hole 89 formed in patient's bone 120. The shockwave delivered by probe 16 is substantially repeatable by instrument 10 when the trigger is thereafter actuated by the surgeon or user such that the orthopedic implant or stem 88 can engage at least portions of void or hole 89, such as sidewalls 83.

Referring now to FIGS. 5(b), 5(d), 6(b) and 6(d), and more particularly to impactor 80 thereof, note that orthopedic impactor 80 may have a mass or weight selected such that surgical instrument 10, probe 16 and orthopedic impactor 80 work in conjunction with one another, and are configured, to provide a shockwave having a predetermined force or falling within a predetermined range of forces that has been determined to be optimal or near-optimal for the particular type and brand of orthopedic implant 82 that is to be used in conjunction with instrument 10. Thus, heavier masses or weights of impactor 80 may be favored for larger implants 82, and conversely lesser weights or masses may be favored for smaller implants 82. By way of example, orthopedic impactor may have a mass or weight ranging between about 3 grams and about 100 grams. Note further that orthopedic impactor 80 may comprise a material or have dimensions or a length selected such that the surgical instrument, the probe and the orthopedic impactor working in conjunction with one another are configured to provide a shockwave having a predetermined force or falling within a predetermined range of forces to the orthopedic implant that has been determined to be optimal or near-optimal for the particular type and brand of orthopedic implant 82 that is to be used in conjunction with instrument 10. Thus, orthopedic impactor 80 may comprise, by way of example, stainless steel, INOX stainless steel, chromium cobalt metal or metal alloys, titanium, suitable biocompatible materials, USP Class VI plastics, or polyetheretherketone (PEEK), or may have a length between its proximal and distal ends ranging between about 2 cm and about 50 cm.

In accordance with the foregoing teachings, the mass or weight, materials and/or dimensions of impactor 80 can be tuned or selected to provide appropriate, suitable and/or optical impact force fine tuning, amplification and/or force reduction with respect to the particular orthopedic implant that is to be used in conjunction with instrument 10. As a result, instrument 10 and its various components can be tuned to impact forces specified by the manufacturer of the orthopedic implant at hand.

Note further that distal end 17 of probe 16, and the probe engagement features of impactor 80 and orthopedic implants 82 and 88 (or to other types of orthopedic implants) may be coated with thin layers of polymers, plastics or other suitable materials such that some degree of protection is provided to ceramic surfaces that are disposed on some types of orthopedic implants, and so that effective forces may be imparted to the implant by instrument 10 without damaging the implant.

According to further embodiments of instrument 10, probe 16, distal end 17, various orthopedic implants such as stem 88 (see, for example, FIGS. 5(a) through 5(d)) or socket 82 (see, for example, FIGS. 6(a) through 6(d)), and/or various embodiments of orthopedic impactor 80 (see, for example, FIGS. 5(b), 5(d), 6(b) and 6(d)), the following features and characteristics are also contemplated: (a) the striker may be disposed within a longitudinal striker sleeve of the instrument; (b) the pneumatic instrument may be configured such that the shockwave provided by the probe has a rise time ranging between about 2 microseconds and about 20 microseconds; (c) the rise time of the instrument may range between about 4 microseconds and about 16 microseconds; (d) the rise time of the instrument may range between about 6 microseconds and about 10 microseconds; (e) the instrument may further comprise a removable probe cap configured to receive the proximal end of the probe therein or therethrough, the probe cap being mountable on the distal end of the instrument; (f) the distal end of the probe may be threaded and configured to threadably engage at least one of the probe engagement feature of the orthopedic implant and the probe engagement feature of the impactor; (g) the distal end of the orthopedic implant impactor may comprise a threaded impactor engagement feature configured to threadably engage and mate with the probe engagement feature of the orthopedic implant; (h) the probe may have a weight or mass ranging between about 15 grams and about 80 grams; (i) the probe may have a length ranging between about 10 centimeters and about 30 centimeters; (j) the pressure regulator may be configured to provide pressurized gas to the trigger mechanism at pressures ranging between about 15 bars and about 60 bars; (k) the pressure regulator may be configured to provide pressurized gas to the trigger mechanism at pressures ranging between about 25 bars and about 35 bars; and (l) the shockwave provided by probe 16 may have a rise time ranging between about 2 microseconds and about 20 microseconds, between about 4 microseconds and about 16 microseconds, between about 6 microseconds and 10 microseconds, or between about 4 microseconds and about 8 microseconds. Note that still other features, characteristics, structural configurations and/or functional attributes are also contemplated, as those skilled in the art will appreciate upon having read and understood the present specification and drawings.

FIG. 8 shows one embodiment of a method 100 for implanting an orthopedic implant with instrument 10. At step 101, the distal end of probe 16, the above-referenced device, or impactor 80 is positioned on a portion of an orthopedic implant that is to be implanted in a patient. At step 103, a shockwave is delivered by instrument 10 to the orthopedic implant by a user actuating the instrument to deliver the shockwave. At step 105, subsequent shockwaves are delivered to the orthopedic implant by instrument 10 as required to effect the desired implantation. According to various embodiments, method 100 may further comprise any one or more of positioning distal end 17 of probe 16, the above-referenced device, or the distal end of impactor 80 in contact with at least a portion of the surface of an orthopedic implant, and actuating trigger mechanism 30 to deliver the shockwave to probe 16 and thence to the orthopedic implant, disposing orthopedic implant impactor 80 on distal end 17 of probe 16 and delivering a shock wave to probe 16, impactor 80, and thence to the orthopedic implant. Note that orthopedic implant 82 and impactor 80 may comprise at least one recess or protrusion or other positive engagement feature disposed thereon or therein that is configured to mateably engage the distal end 17 of probe 16.

In yet further embodiments, an orthopedic implant system is provided comprising an orthopedic implant, pneumatic surgical instrument 10 disclosed and described herein, removable probe 16, and the above-described orthopedic implant impactor 80. In still further embodiments, an orthopedic implant is provided that is configured to operate in conjunction with surgical instrument 10, probe 16, and/or impactor 80 such that the orthopedic implant may be implanted in a patient's bone using surgical instrument 10.

Orthopedic implants manufactured and sold by Stryker™, DePuy Medical™, Biomed™, Zimmer™, Smith & Nephew™, Wright Medical™, and numerous other manufacturers may be modified in accordance with the teachings described herein. Other orthopedic implants that may be modified in accordance with the teachings set forth herein and that would be suitable for use with surgical instrument 10 include, but are not limited to, spinal cages, knee implants, and other orthopedic implants not specifically enumerated herein.

Figure 9A:
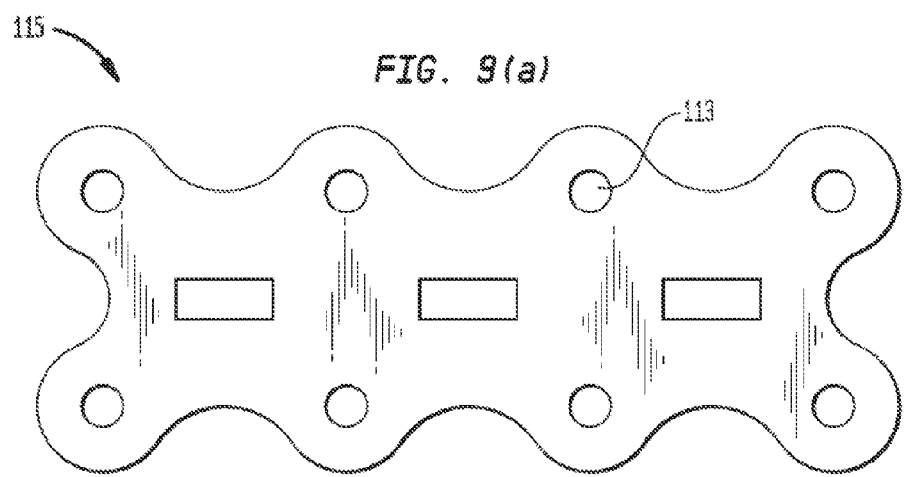
FIG. 9(a) shows one embodiment of a bone plate 115.
Figure 9B:
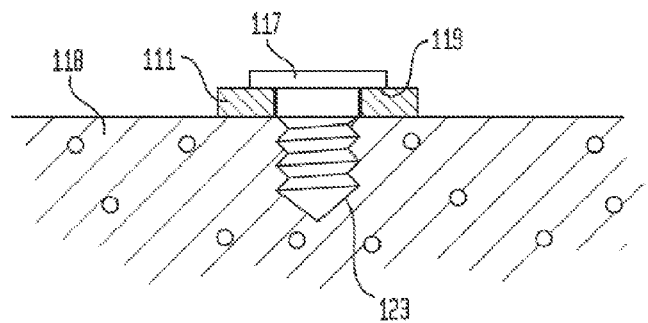
FIG. 9(b) shows one embodiment of bone screw 117 in bone 118 to secure bone plate 115 thereto.
Figure 9C:
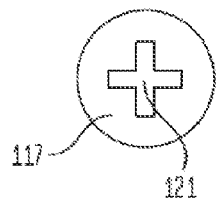
FIG. 9(c) shows a top plan view of one embodiment of bone screw 117.
Figure 9D:
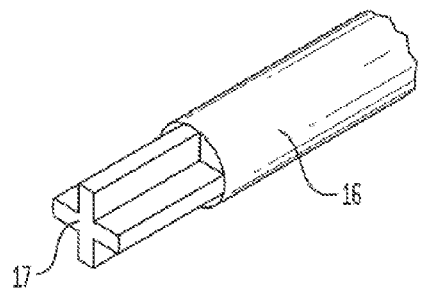
FIG. 9(d) shows one embodiment of a distal end 17 of probe 16 configured to engage screw 117.

Referring now to FIG. 9(a), there is shown one embodiment of a metallic bone plate 115 comprising screw holes 113. FIG. 9(b) shows bone plate 115 attached to patient's bone 118 by means of screw 117, which aids in securing bone plate 115 thereto. At junction 119 between the bottom of the screw head of screw 117 and the top surface of bone plate 115, corrosion can develop, typically through galvanic action or potentials arising from the disparate metals employed to form screw 117 and bone plate 115. Such corrosion can essentially lock bone plate 115 to screws 117 and cause difficulty in the removal of screws 117 if bone plate 115 is to be removed from the patient, or replaced or repositioned. FIG. 9(c) shows a top plan view of one embodiment of bone screw 117, and 9(d) shows one embodiment of a distal end 17 of probe 16 configured to engage slots 121 in screw 117. Instrument 10 and probe 16 can be employed to deliver a shock wave to screw 117 using probe 16 of the type shown in FIG. 9(d), and thereby loosen screw 117 from bone plate 115 as a result of the bonds between the aforementioned corrosion and screw 117 and bone plate 115. Other types of screws, screw slots, and distal ends 17 other than those shown explicitly in FIGS. 9(b) through 9(d) are also contemplated for use in conjunction with surgical instrument 10, as those skilled in the art will now understand. Moreover, surgical instrument 10 may also be employed to remove bone plates for massive bone reconstruction.

The above-described embodiments should be considered as examples of the present invention, rather than as limiting the scope of the invention. In addition to the foregoing embodiments of the invention, review of the detailed description and accompanying drawings will show that there are other embodiments of the present invention. Accordingly, many combinations, permutations, variations and modifications of the foregoing embodiments of the present invention not set forth explicitly herein will nevertheless fall within the scope of the present invention.

We claim:

1. A pneumatic surgical instrument, comprising:
   a striker;
   a removable probe mountable on a distal end of the instrument;
   at least one removable probe cap configured to receive a proximal end of the removable probe therein or therethrough, the probe cap being mountable on the distal end of the surgical instrument;
   at least one removable O-ring disposed between an inner surface of the probe cap and a distal terminus of the removable probe;
   a pressure regulator operably connectable to a self-contained gas cartridge mountable on or in the instrument, and
   a trigger mechanism comprising a trigger, the trigger mechanism being operably connected to the pressure regulator and to the striker;
   wherein the probe has a distal end configured and shaped to engage or to be secured in or on a probe engagement feature disposed: (a) in or an orthopedic implant; or (b) in or on an orthopedic implant impactor configured to matingly engage the orthopedic implant, wherein the surgical instrument is configured: (a) to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and thence into the orthopedic implant or into the orthopedic impactor and the orthopedic implant; (b) to drive the orthopedic implant at least partially into a void or hole formed in a patient's bone; (c) such that the shockwave delivered by the probe is substantially repeatable when the trigger is thereafter actuated by the user such that the instrument is configured to cause the orthopedic implant to engage at least portions of the void or hole in the bone; and (d) such that the shockwave provided by the probe has a rise time ranging between about 2 microseconds and about 20 microseconds; and further wherein the at least one O-ring is selectable according to a thickness, mechanical properties, materials, or stiffness of the O-ring, and the at least one probe cap is selectable such that internal dimensions of the at least one probe cap are configured, thereby to provide a given amount of relative displacement between the probe and the instrument body when the instrument is triggered or actuated, and wherein selection of a different one of the at least one O-ring and/or at least one cap provides the probe with a different relative displacement as compared with a selection of another of the at least one cap and/or at least one O-ring.

2. The pneumatic surgical instrument of claim 1, wherein the O-ring comprises nitrile.

3. The pneumatic surgical instrument of claim 1, wherein the probe O-ring has a thickness ranging between about 1 mm and about 6 mm.

4. The pneumatic surgical instrument of claim 1, wherein the probe O-ring has a thickness ranging between about 2 mm and about 4 mm.

5. The pneumatic surgical instrument of claim 1, wherein the probe further comprises a shaft having the probe terminus disposed at a proximal end thereof.

6. The pneumatic surgical instrument of claim 5, wherein the removable probe cap is configured to receive the shaft therethrough and to house proximally therefrom within the instrument the at least one probe O-ring disposed against a distal surface of the proximal probe terminus.

7. The pneumatic surgical instrument of claim 1, wherein the distal end of the probe is threaded and configured to threadably engage at least one of the probe engagement feature of the orthopedic implant and the probe engagement feature of the impactor.

8. The pneumatic surgical instrument of claim 1, wherein the distal end of the orthopedic implant impactor comprises a threaded impactor engagement feature configured to threadably engage and mate with the probe engagement feature of the orthopedic implant.

9. The pneumatic surgical instrument of claim 1, wherein the orthopedic impactor has a mass or weight selected such that the surgical instrument, the probe and the orthopedic impactor working in conjunction with one another are configured to provide a shockwave having a predetermined force or falling within a predetermined range of forces to the orthopedic implant.

10. The pneumatic surgical instrument of claim 1, wherein the orthopedic impactor comprises a material or has dimensions selected such that the surgical instrument, the probe and the orthopedic impactor working in conjunction with one another are configured to provide a shockwave having a predetermined force or falling within a predetermined range of forces to the orthopedic implant.

11. The pneumatic surgical instrument of claim 1, wherein the orthopedic impactor comprises one of stainless steel, INOX stainless steel, chromium cobalt metal or metal alloys, titanium, suitable biocompatible materials, USP Class VI plastics, and polyetheretherketone (PEEK).

12. The pneumatic surgical instrument of claim 1, wherein the orthopedic impactor has a mass or weight ranging between about 3 grams and about 100 grams.

13. The pneumatic surgical instrument of claim 1, wherein the orthopedic impactor has a length between its proximal and distal ends ranging between about 3 cm and about 50 cm.

14. The pneumatic surgical instrument of claim 1, wherein the probe has a weight or mass ranging between about 15 grams and about 80 grams.

15. The pneumatic surgical instrument of claim 1, wherein the probe has a length ranging between about 10 centimeters and about 30 centimeters.

16. The pneumatic surgical instrument of claim 1, wherein the pressure regulator is further configured to provide pressurized gas to the trigger mechanism at pressures ranging between about 15 bars and about 60 bars.

17. The pneumatic surgical instrument of claim 1, wherein the pressure regulator is further configured to provide pressurized gas to the trigger mechanism at pressures ranging between about 25 bars and about 35 bars.

18. An orthopedic implant system, comprising:
an orthopedic implant;
a pneumatic surgical instrument comprising a striker, a removable probe mountable on a distal end of the instrument, at least one removable probe cap configured to receive a proximal end of the removable probe therein or therethrough, the probe cap being mountable on the distal end of the surgical instrument, at least one removable O-ring disposed between an inner surface of the probe cap and a distal terminus of the removable probe, a pressure regulator operably connectable to a self-contained gas cartridge mountable on or in the instrument, and a trigger mechanism comprising a trigger, the trigger mechanism being operably connected to the pressure regulator and to the striker, the probe having a distal end configured and shaped to engage or to be secured in or on a probe engagement feature disposed: (a) in or the orthopedic implant; or (b) in or on an orthopedic implant impactor configured to matingly engage the orthopedic implant, and the pneumatic surgical instrument is configured: (a) to deliver at least one shock wave to the probe when the trigger is actuated by a user and a predetermined volume of gas stored at a predetermined range of pressures in the instrument is released thereby to cause the striker to move towards a distal end of the instrument and deliver the shock wave to the proximal end of the probe and thence into the orthopedic implant or into the orthopedic impactor and the orthopedic implant, (b) to drive the orthopedic implant at least partially into a void or hole formed in a patient's bone; (c) such that the shockwave delivered by the probe is substantially repeatable when the trigger is thereafter actuated by the user such that the instrument is configured to cause the orthopedic implant to engage at least portions of the void or hole in the bone; and (d) such that the shockwave provided by the probe has a rise time ranging between about 2 microseconds and about 20 microseconds; and further wherein the at least one O-ring is selectable according to a thickness, mechanical properties, materials, or stiffness of the O-ring, and the at least one probe cap is selectable such that internal dimensions of the at least one probe cap are configured, thereby to provide a given amount of relative displacement between the probe and the instrument body when the instrument is triggered or actuated, and wherein selection of a different one of the at least one O-ring and/or at least one cap provides the probe with a different relative displacement as compared with a selection of another of the at least one cap and/or at least one O-ring.

19. The orthopedic implant system of claim 18, wherein the orthopedic implant is one of an orthopedic hip implant socket, an orthopedic hip implant stem, an orthopedic shoulder implant socket, and an orthopedic shoulder implant stem.

* * * * *